US010098612B2

United States Patent
Shiotani et al.

(10) Patent No.: US 10,098,612 B2
(45) Date of Patent: Oct. 16, 2018

(54) ULTRASOUND UNIT AND ULTRASOUND ENDOSCOPE

(71) Applicant: OLYMPUS CORPORATION, Tokyo (JP)

(72) Inventors: Koichi Shiotani, Hachioji (JP); Hideharu Miyahara, Nagano (JP); Kazuya Matsumoto, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 754 days.

(21) Appl. No.: 14/629,588

(22) Filed: Feb. 24, 2015

(65) Prior Publication Data

US 2015/0164470 A1   Jun. 18, 2015

Related U.S. Application Data

(63) Continuation of application No. PCT/JP2013/061387, filed on Apr. 17, 2013.

(30) Foreign Application Priority Data

Sep. 7, 2012   (JP) .................................. 2012-197407

(51) Int. Cl.
 *B06B 1/02* (2006.01)
 *A61B 8/12* (2006.01)
 *A61B 8/00* (2006.01)

(52) U.S. Cl.
 CPC ................ *A61B 8/12* (2013.01); *A61B 8/445* (2013.01); *A61B 8/4444* (2013.01);
 (Continued)

(58) Field of Classification Search
 CPC ......... A61B 8/12; A61B 8/4488; A61B 8/445; A61B 8/4444; A61B 8/54; A61B 8/4483; B06B 1/0292
 See application file for complete search history.

(56) References Cited

U.S. PATENT DOCUMENTS 8,047,995 B2   11/2011   Wakabayashi et al.
2008/0089180 A1   4/2008   Matsumoto et al.
(Continued)

FOREIGN PATENT DOCUMENTS

EP   1911529 A1   4/2008
EP   1 932 479 A1   6/2008
(Continued)

OTHER PUBLICATIONS

Extended Supplementary European Search Report dated May 30, 2016 in related European Application No. 13 83 5242.2.
(Continued)

*Primary Examiner* — Elmer Chao
(74) *Attorney, Agent, or Firm* — Scully, Scott, Murphy & Presser, P.C.

(57) ABSTRACT

An ultrasound unit includes: ultrasound elements each including a plurality of ultrasound cells formed on a substrate including a semiconductor, the plurality of ultrasound cells each including an upper electrode having a ground potential and a lower electrode to which a drive signal is applied, the upper electrode and the lower electrode being arranged facing each other via a cavity and thereby forming a first capacitor; a package member in which the plurality of ultrasound elements are disposed, the package member having a ground potential; and an insulation member disposed between the package member and each of the ultrasound elements. A second capacitor is formed as a result of the insulation member serving as a gap, and a capacity of a third capacitor serially connected to the second capacitor is smaller than a capacity of the second capacitor.

10 Claims, 6 Drawing Sheets

(52) U.S. Cl.
CPC .............. *A61B 8/4483* (2013.01); *A61B 8/54* (2013.01); *B06B 1/0292* (2013.01)

(56) References Cited

U.S. PATENT DOCUMENTS

| | | |
|---|---|---|
| 2008/0089181 A1 | 4/2008 | Adachi et al. |
| 2009/0204004 A1 | 8/2009 | Adachi et al. |

FOREIGN PATENT DOCUMENTS

| | | |
|---|---|---|
| EP | 2030698 A1 | 3/2009 |
| EP | 2 168 493 A1 | 3/2010 |
| JP | 2006-050314 A | 2/2006 |
| JP | 2008-093214 A | 4/2008 |
| JP | 2008-099036 A | 4/2008 |
| JP | 2008-118631 A | 5/2008 |
| JP | 2009-050560 A | 3/2009 |
| JP | 2009-055473 A | 3/2009 |
| WO | WO 2008/044727 A1 | 4/2008 |

OTHER PUBLICATIONS

International Search Report dated May 21, 2013 issued in PCT/JP2013/061387.

ULTRASOUND UNIT AND ULTRASOUND ENDOSCOPE

CROSS REFERENCE TO RELATED APPLICATION

This application is a continuation application of PCT/JP2013/061387 filed on Apr. 17, 2013 and claims benefit of Japanese Application No. 2012-197407 filed in Japan on Sep. 7, 2012, the entire contents of which are incorporated herein by this reference.

BACKGROUND OF THE INVENTION

1. Field of the Invention

The present invention relates to an ultrasound unit in which ultrasound elements each including capacitive micromachined ultrasound cells formed on a semiconductor substrate are disposed on a package member via an insulation member, and an ultrasound endoscope including the ultrasound unit.

2. Description of the Related Art

Ultrasound diagnosis in which a diagnosis is made by applying ultrasound to an object to be examined to form an image of a state of the inside of the body from echo signals is widespread. An ultrasound endoscope system is one of diagnostic apparatuses used for ultrasound diagnosis. An ultrasound endoscope includes an ultrasound unit disposed at a distal end portion of an insertion portion to be inserted into a body. The ultrasound unit has a function that converts electric signals to ultrasound and transmits the ultrasound to the inside of the body and receives the ultrasound reflected by the inside of the body and converts the ultrasound to electric signals.

As an ultrasound cell for an ultrasound unit, Japanese Patent Application Laid-Open Publication No. 2006-50314 discloses a capacitive micro-machined ultrasonic transducer (cMUT) manufactured using an MEMS technique.

An ultrasound cell for a cMUT transmits/receives ultrasound by means of vibration of a membrane including an upper electrode arranged facing a lower electrode via a cavity. In transmission, upon application of a voltage between the electrodes, the upper electrode is pulled to the lower electrode by an electrostatic force, whereby the membrane including the upper electrode is deformed. When the voltage application ceases, the membrane recovers to its original shape by means of an elastic force. Ultrasound is generated by the deformation/recovery of the membrane.

On the other hand, in reception, the membrane is deformed by received ultrasound energy, whereby a distance between the upper electrode and the lower electrode changes. Using a change of a capacity C1 of a capacitor formed by the upper electrode and the lower electrode by $\Delta C$, the received ultrasound energy is converted to an electric signal.

SUMMARY OF THE INVENTION

An ultrasound unit according to an embodiment of the present invention includes: ultrasound elements each including a plurality of ultrasound cells formed on a substrate including a semiconductor, the plurality of ultrasound cells each including an upper electrode having a ground potential and a lower electrode to which a drive signal is applied, the upper electrode and the lower electrode being arranged facing each other via a cavity and thereby forming a first capacitor; a package member in which the plurality of the ultrasound elements are disposed, the package member having a ground potential; and an insulation member disposed between the package member and each of the ultrasound elements. A second capacitor is formed as a result of the insulation member serving as a gap, and a capacity of a third capacitor serially connected to the second capacitor is smaller than a capacity of the second capacitor.

Also, an ultrasound endoscope according to another embodiment includes: an insertion portion including a distal end portion in which an ultrasound unit is disposed, the ultrasound unit including ultrasound elements each including a plurality of ultrasound cells formed on a substrate including a semiconductor, the plurality of ultrasound cells each including an upper electrode having a ground potential and a lower electrode to which a drive signal is applied, the upper electrode and the lower electrode being arranged facing each other via a cavity and thereby forming a first capacitor, a package member in which the plurality of the ultrasound elements are disposed, the package member having a ground potential, and an insulation member disposed between the package member and each of the ultrasound elements, in which a second capacitor is formed as a result of the insulation member serving as a gap and a capacity of a third capacitor serially connected to the second capacitor is smaller than a capacity of the second capacitor; an operation portion disposed on a proximal end portion side of the insertion portion; and a universal cord provided so as to extend from the operation portion.

DETAILED DESCRIPTION OF THE PREFERRED EMBODIMENTS

<First Embodiment>

An ultrasound unit 30 and an ultrasound endoscope 2 including the ultrasound unit 30 (hereinafter referred to as "ultrasound unit 30 and the like") according to a first embodiment will be described with reference to the drawings. Note that each of the drawings is a schematic diagram for description and, e.g., counts and sizes of components and ratios in size among the components are different from those of actual ones.

<Configuration of Ultrasound Endoscope>

Figure 1:
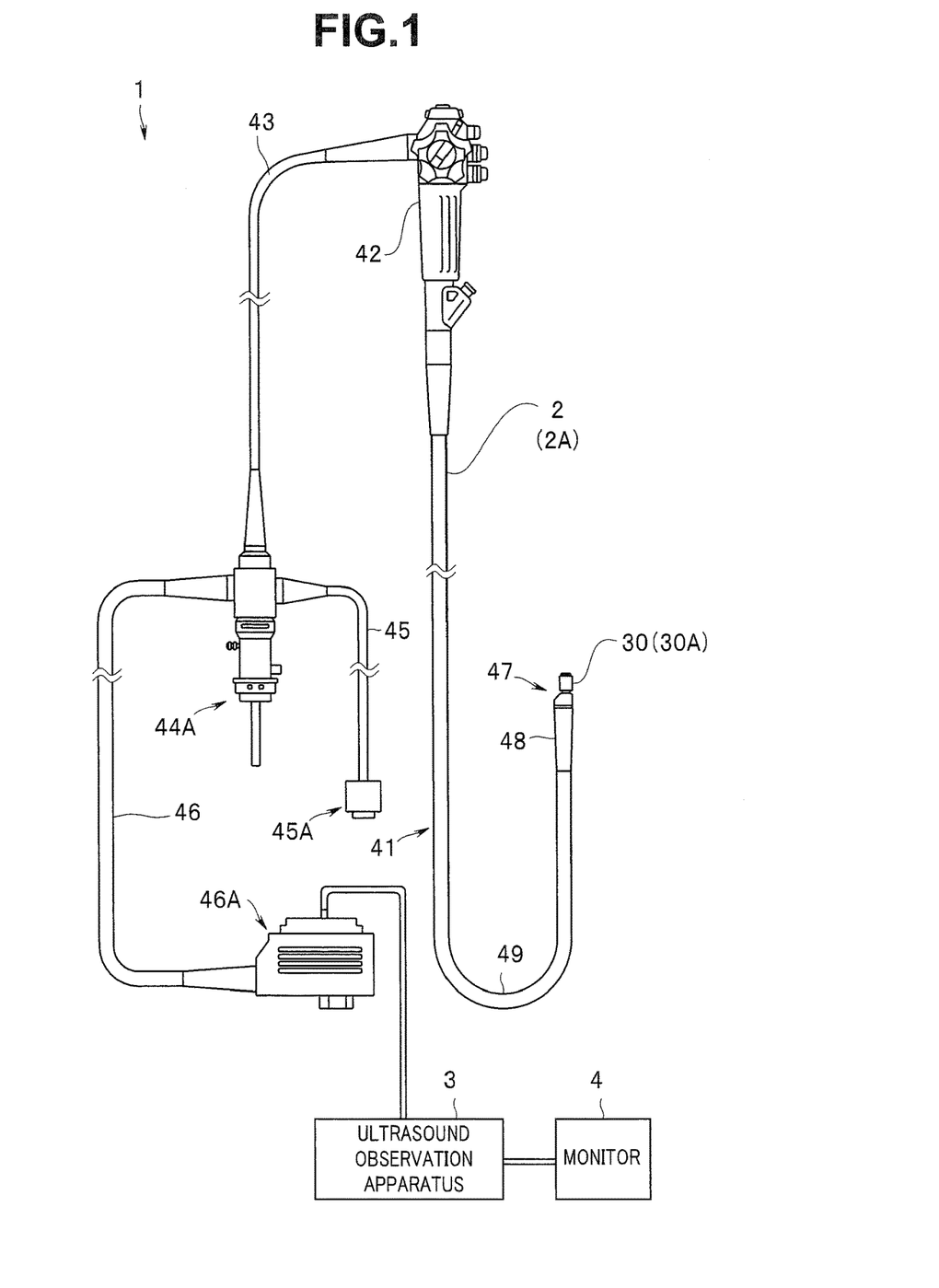
FIG. 1 is a diagram of a configuration of an endoscope system including an ultrasound endoscope according to an embodiment.

As illustrated in FIG. 1, the ultrasound endoscope 2 provides an ultrasound endoscope system 1 jointly with an ultrasound observation apparatus 3 and a monitor 4. The ultrasound endoscope 2 includes an elongated insertion portion 41 to be inserted into a body, an operation portion 42 disposed at a proximal end of the insertion portion 41, and a universal cord 43 extending from the operation portion 42.

A connector 44A to be connected to a light source apparatus (not illustrated) is disposed at a proximal end portion of the universal cord 43. A cable 45 to be connected to a camera control unit (not illustrated) via a connector 45A, and a cable 46 to be connected to the ultrasound observation apparatus 3 via a connector 46A extend from the connector 44A. The monitor 4 is connected to the ultrasound observation apparatus 3.

The insertion portion 41 is provided by providing a distal end rigid portion (hereinafter referred to as "distal end portion") 47, a bending portion 48 positioned at a rear end of the distal end portion 47 and a flexible tube portion 49 positioned at a rear end of the bending portion 48, the flexible tube portion 49 having a small diameter, a long length and flexibility and leading to the operation portion 42, consecutively in this order from the distal end side.

Figure 2:
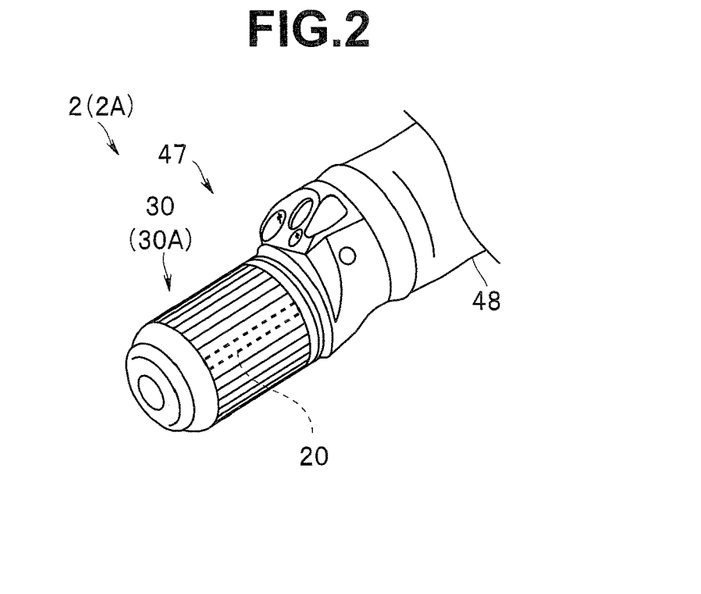
FIG. 2 is a perspective view of a distal end portion of the ultrasound endoscope according to the embodiment.

As illustrated in FIG. 2, in the distal end portion 47 of the insertion portion 41, the ultrasound unit 30 in which a plurality of ultrasound elements 20 are radially arranged is disposed. Note that the ultrasound unit may be of a convex scanning type in which a plurality of ultrasound elements 20 are arranged in a convex shape or of a linear scanning type in which a plurality of ultrasound elements 20 are arranged on a planar surface.

<Configuration of Ultrasound Unit>

Next, a configuration of the ultrasound unit 30 will be described with reference to FIGS. 3, 4 and 5. Note that in FIG. 4, etc., a package member 60 is illustrated in a flat plate shape.

Figure 3:
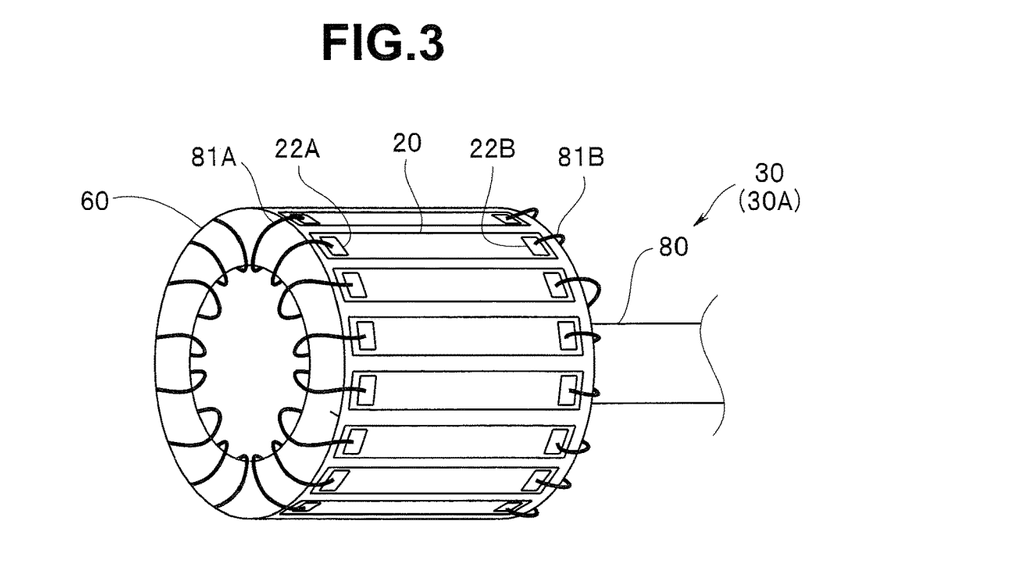
FIG. 3 is a perspective view of an ultrasound unit according to the embodiment.

As illustrated in FIG. 3, the ultrasound unit 30 is a radial transducer in which a plurality of ultrasound elements 20 each having a rectangular shape in plan view are cylindrically arranged at regular intervals on an outer circumferential face of the package member 60 having a cylindrical shape in such a manner that long sides of the ultrasound elements 20 are parallel to one another.

Figure 4:
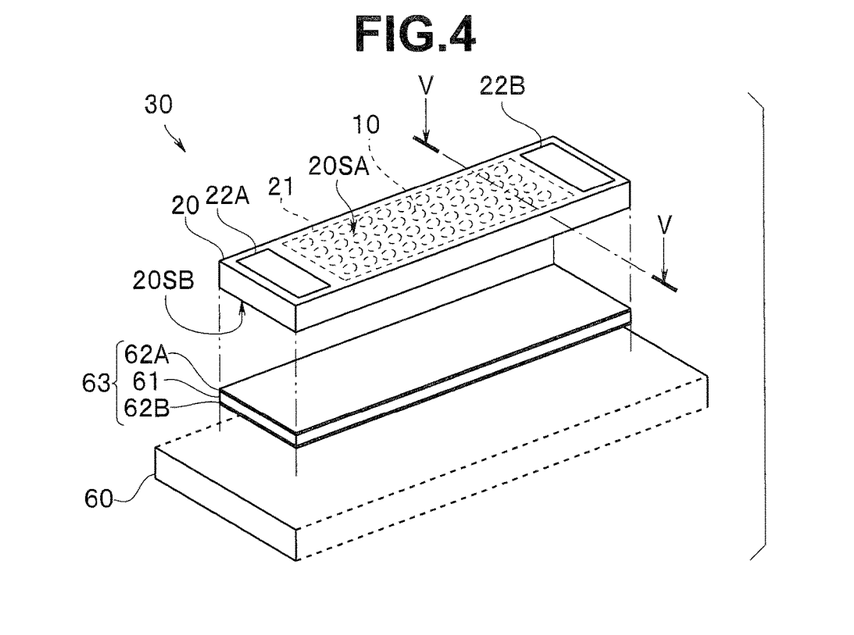
FIG. 4 is an exploded view of the ultrasound unit according to the embodiment.

As illustrated in FIG. 4, an insulation member 63 including a backing material 61 and joining layers 62A and 62B are disposed between each ultrasound element 20 and the package member 60. Each ultrasound element 20, which is a basic unit that transmits/receives ultrasound, includes a silicon substrate (substrate) 11 as a base, the silicon substrate 11 including a first principal surface 20SA and a second principal surface 20SB facing the first principal surface 20SA. In a roughly center portion of the first principal surface 20SA of the ultrasound element 20, a transmission/reception section 21 that transmits/receives ultrasound is formed, and in opposite end portions of the first principal surface 20SA, respective external electrodes 22A and 22B are disposed. As illustrated in FIG. 3, the external electrodes 22A and 22B are connected to respective lead wires 81A and 81B of cables 80. The lead wires 81B are ground potential wires and may be a common wiring for the plurality of ultrasound elements 20. For example, shield wires of the cable 80 can be used as the lead wires 81B.

The cable 80 is inserted through the distal end portion 47, the bending portion 48, the flexible tube portion 49, the operation portion 42, the universal cord 43 and the cable 46, and is connected to the ultrasound observation apparatus 3 via the connector 46A.

In the transmission/reception section 21, a plurality of capacitive micro-machined ultrasound cells 10 are arranged in a matrix. Note that FIG. 4 schematically illustrates only a part of the ultrasound cells 10. Also, the ultrasound cells 10 may be arranged in such a manner that the ultrasound cells 10 are fitted in a recess portion formed in the package member 60.

Figure 5:
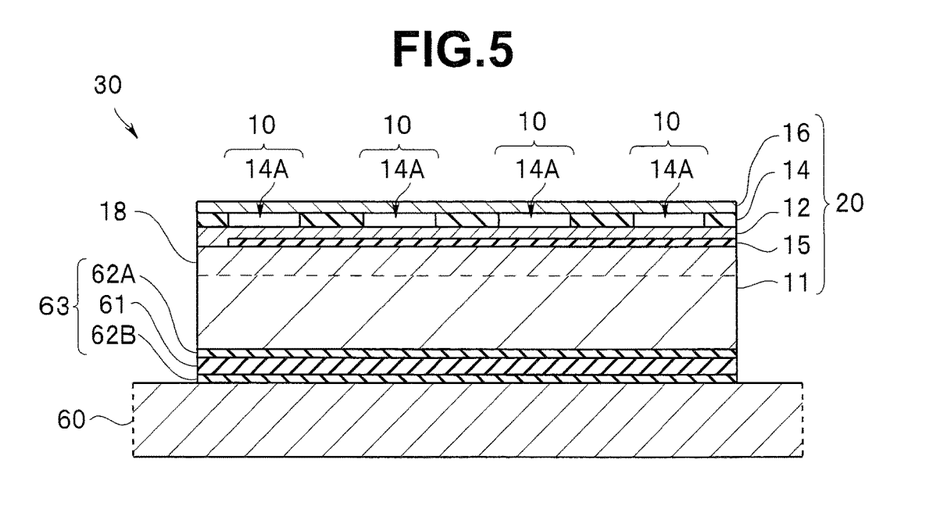
FIG. 5 is a cross-sectional view of the ultrasound unit according to the first embodiment along line V-V in FIG. 4.

As illustrated in FIG. 5, in each of the ultrasound cells 10 formed on the silicon substrate 11, an upper electrode 16, which is included in a membrane, is arranged facing a lower electrode 12 via a cavity (void portion) 14A. The cavity (void portion) 14A is formed by etching of an interelectrode insulation layer 14. Note that an upper insulation layer and a protection film, which are not illustrated, are formed on the upper electrode 16.

Also, on a surface of the silicon substrate 11 including a semiconductor, an insulation layer 15 including silicon oxide is formed; however, the insulation layer 15 includes through holes and thus the lower electrode 12 and the silicon substrate are electrically connected. In other words, the insulation layer 15 can be regarded as being virtually not formed.

Note that the external electrode 22A of the ultrasound element 20 is a common electrode for the lower electrode 12 of the plurality of ultrasound cells 10, and the external electrode 22B is a common electrode for the upper electrode 16 of the plurality of ultrasound cells 10. Thus, the plurality of ultrasound cells 10 included in one ultrasound element 20 is simultaneously driven.

The package member 60 is a conductive member including a conductive material such as stainless steel. The package member 60 may be a conductive member including a conductive layer formed on at least one surface of a non-conductive base material such as a resin. For safety, a conductive member to be inserted into a living body is maintained at the ground potential. In other words, the package member 60 is maintained at the ground potential, as with the upper electrodes 16, via a non-illustrated lead wire. The package member 60 may be connected to the lead wires 81B that maintain the upper electrodes 16 at the ground potential.

The plurality of ultrasound elements 20 are disposed on the outer circumferential face of the package member 60 by the respective joining layers 62 (62A and 62B) via the respective backing materials 61.

For the backing materials 61 that absorb unnecessary ultrasound, any of various materials can be used and either an inorganic material or an organic material can be employed. In particular, a material obtained by mixing a filler into an epoxy-based resin or a rubber-based material having a large attenuation rate is preferable because such material can effectively absorb unnecessary vibration. For the filler, it is preferable to use a material having a density that is higher than that of the epoxy resin or the rubber-based material, which is a matrix material, because such material can further effectively attenuate unnecessary vibration. Also, for the joining layers 62 (62A and 62B), it is preferable to use, e.g., an epoxy-based adhesive containing 0.5 to 2% of a silane coupling agent.

The backing material 61 and the joining layers 62A and 62B, which each include an elastic member, are all insulating materials, and can be regarded as one insulation member 63 as a whole. The insulation member 63 may arbitrarily be set according to the materials, sizes and the like of the respective components, for example, in such a manner that a thickness of the backing material 61 is set to 50 to 200 μm and respective thicknesses of the joining layers 62A and 62B are set to 0.5 to 2.0 μm. Also, a structure that does not have three joining layers, that is, uses no backing material 61 may be employed, and in this case, an unitary insulation member 63 is made to have a thickness that is equal to or exceeds a thickness enough to ensure insulation required for driving the ultrasound element 20 for transmission/reception.

Then, at the surface of the silicon substrate 11, a diffusion layer 18 having a polarity that is different from that of a parent material of the substrate and having a resistance that is lower than that of the parent material is formed. For example, if the parent material of the silicon substrate 11 is a p-type semiconductor (p-semiconductor) containing a triad such as boron, a pentad such as phosphorus is doped from the first principal surface 20SA and an n-type diffusion layer (n+ semiconductor) 18 is formed on the surface. The diffusion layer 18 has an impurity density that is higher than that of the parent material of the silicon substrate 11. In other words, the parent material of the silicon substrate 11 has an electric resistance that is higher than that of the diffusion layer 18.

<Operation of Ultrasound Unit>

In ultrasound transmission, a drive signal (voltage) is applied to the lower electrodes 12 via the lead wires 81B and the external electrodes 22A by the control performed by the ultrasound observation apparatus 3. For example, in the case of an n+ diffusion layer and a p-substrate, a positive drive voltage that is higher than the ground potential is applied. On the other hand, in the case of a p+ diffusion layer and an n-substrate, a negative drive voltage that is lower than the ground potential is applied. The upper electrode 16 and the package member 60 are maintained at the ground potential. Note that, in the ultrasound endoscope 2, the upper electrode 16, which is close to the outside, has the ground potential, and thus, the ultrasound endoscope 2 is safer than endoscopes that allow a voltage to be applied to upper electrodes 16.

On the other hand, in ultrasound reception, the capacities C1 between the lower electrodes 12 and the upper electrodes 16 are measured via the respective external electrodes 22A and 22B by the control performed by the ultrasound observation apparatus 3. In other words, a capacity change ΔC of each first capacitor 71 formed by the relevant lower electrode 12 and the relevant upper electrode 16 with the relevant cavity 14A serving as a gap. In this case, it is preferable that a bias voltage be applied to the lower electrodes 12. The bias voltage has a polarity that is the same as that of the drive voltage.

Figure 6:
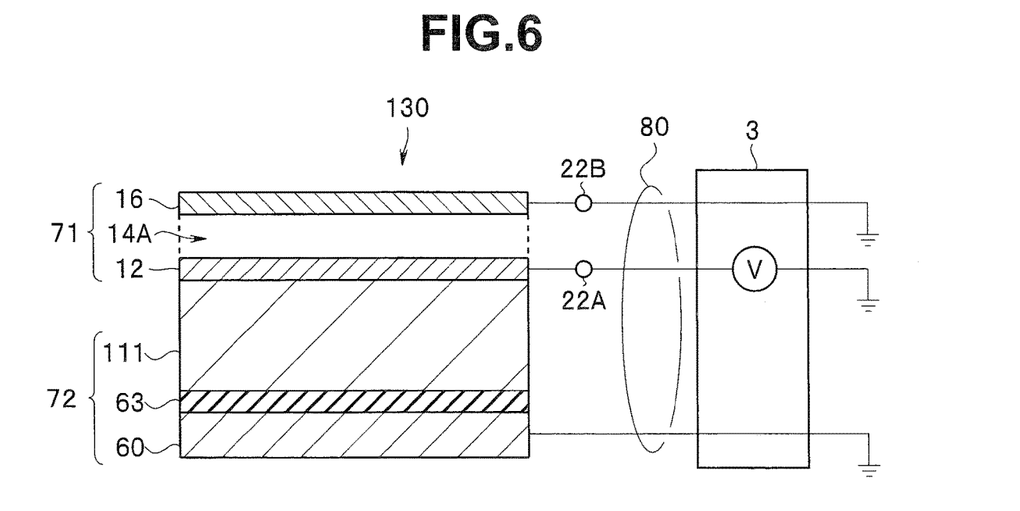
FIG. 6 is a diagram illustrating a configuration of a conventional ultrasound unit.
Figure 7:
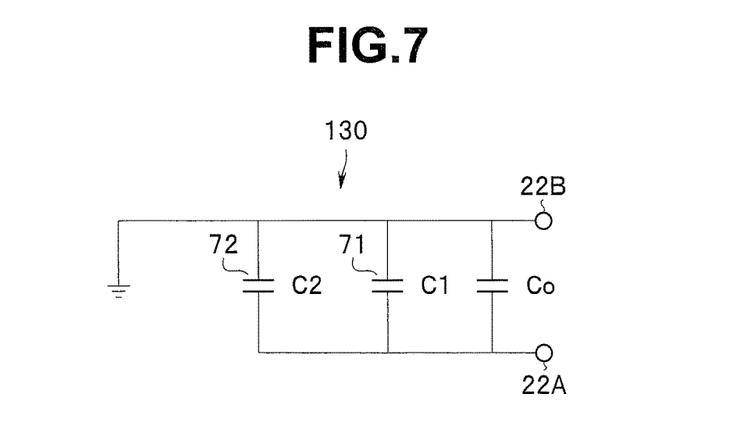
FIG. 7 is a diagram of an equivalent circuit in the conventional ultrasound unit.

As illustrated in FIGS. 6 and 7, in a conventional ultrasound unit 130, a second capacitor 72 having a capacity C2, which is formed between a silicon substrate 111 (lower electrode 12) and a package member 60 with an insulation member 63 serving as a gap, is connected in parallel to a first capacitor 71. Furthermore, an overlap region in which an interelectrode insulation layer 14 is interposed between the lower electrode 12 and an upper electrode 16 provides a parasitic capacity whose capacity value does not change, and a sum of a capacity Co of the overlap region and C2 is a total parasitic capacity Cp.

As a result, as already described, if the capacity of the first capacitor 71 changes by ΔC, the capacity change rate D (%) measured via external electrodes 22A and 22B decreases from ΔC/C1 to ΔC/(C1+Cp) because of the total parasitic capacity Cp. Note that for the below numeric value calculation (estimation), Co is regarded as sufficiently small compared to the other capacities. In other words, it is regarded that Cp=C2; however, even if Cp>C2, the embodiment exerts sufficient effects.

For example, where C1=13 pF, C2=5.3 pF and ΔC=1.3 pF, the capacity change rate D decreases from 10.0% to 7.1%.

Figure 8:
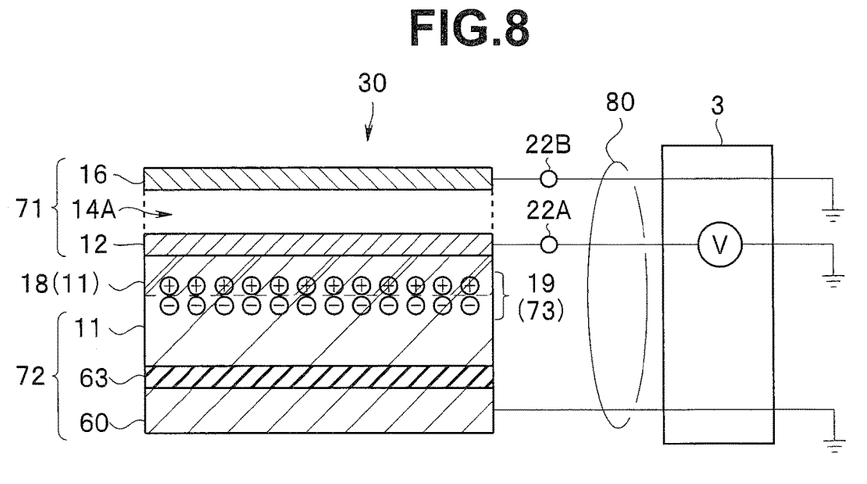
FIG. 8 is a diagram illustrating a configuration of the ultrasound unit according to the first embodiment.
Figure 9:
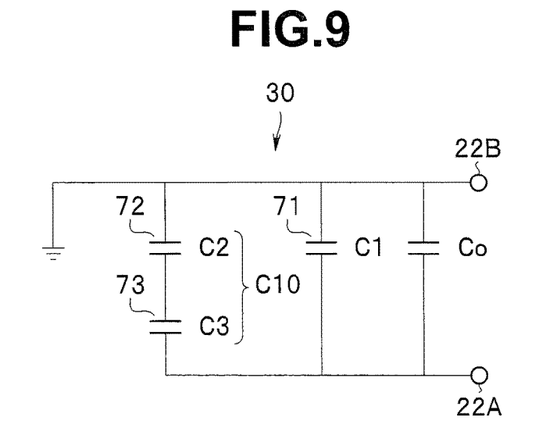
FIG. 9 is a diagram of an equivalent circuit in the ultrasound unit according to the first embodiment.

On the other hand, as illustrated in FIGS. 8 and 9, in the ultrasound unit 30, upon application of a positive voltage to the lower electrode 12, a potential of the diffusion layer 18 becomes a positive potential, whereby electrons move to the diffusion layer side of the silicon substrate 11. As a result, a depletion layer 19 is formed inside the silicon substrate 11. Since the depletion layer 19 has no conductivity, a third capacitor 73 in which the depletion layer 19 serves as a gap is formed.

Here, a thickness of the depletion layer 19, that is, a gap length of the third capacitor 73 is nearly 500 μm where the silicon substrate 11, which is a p-semiconductor, has an acceptor density of $5 \times 10^{11}$ cm$^{-3}$, the diffusion layer 18, which is an n+semiconductor, has a donor density of $5 \times 10^{19}$ cm$^{-3}$, and an applied voltage is 100V. Thus, where the depletion layer 19 has a permittivity of 11.9, a capacity C3 of the third capacitor 73 is 1.2 pF.

As illustrated in FIG. 9, the third capacitor 73 is serially connected to a second capacitor 72 having a capacity C2, which is formed as a result of the insulation member 63 serving as a gap, and a sum of the capacities C2 and C3 and a capacity Co of an overlap region is a total parasitic capacity Cp. A combined capacity C10 of the second capacitor 72 and the third capacitor 73 serially connected can be obtained by C10=(C2×C3)/(C2+C3). In other words, C2>C10. Here, also, Co is regarded as sufficiently small compared to the other capacities, and it is regarded as Cp=C10; however, implementation of the present invention is not limited to such calculation method as above.

In other words, where the second capacitor 72 and the third capacitor 73 are serially connected, the combined capacity C10 becomes smaller than each of the capacity C2 of the second capacitor 72 and the capacity C3 of the third capacitor 73, and the capacity of the capacitor having a smaller capacity becomes dominant. Here, the capacity C3 of the third capacitor 73 is smaller than the capacity C2 of the second capacitor 72. Thus, C2>C10.

Since the parasitic capacity Cp decreases from C2 to C10, if the capacity of the first capacitor 71 changes by ΔC, the capacity change rate D (%) measured via the external electrodes 22A and 22B increases from ΔC/(C1+C2) to ΔC/(C1+C10) compared to cases where no third capacitor 73 is formed.

For example, where C1=13 pF, C2=5.3 pF, C3=1.2 pF and ΔC=1.3 pF, the capacity change rate D increases from 7.1% to 9.3%.

As described above, the ultrasound unit 30 includes ultrasound elements 20 in which the diffusion layer 18 having a polarity that is different from that of the parent material of a silicon substrate 11 and having a resistance that is lower than that of the parent material is formed at the surface of the substrate 11 and the third capacitor 73 is formed, with the depletion layer 19 serving as a gap, the depletion layer 19 being formed inside the substrate 11 by the diffusion layer 18. The ultrasound 30 thus configured has high receiving sensitivity.

Note that if a negative voltage is applied to the lower electrode 12, effects that are the same as those of the ultrasound unit 30 can be provided by making the silicon substrate be an n-semiconductor and making the diffusion layer be a p+ semiconductor.

Although the capacity C3 of the third capacitor is selected in connection with the capacity C2 of the second capacitor, for further sensitivity enhancement, preferably C3≤0.5×C2, more preferably, C3≤0.1×C2.

As described above, for reduction of the parasitic capacity Cp, it is only necessary that the third capacitor be serially connected to the second capacitor formed as a result of the insulation member 63 serving as a gap. Thus, not only a method in which a diffusion layer 18 is formed in advance so as to form a third capacitor inside the silicon substrate 11, but also, for example, a third capacitor may be formed by disposing a capacitor component having a small capacity at a position halfway through the ground potential wire to which the package member 60 is connected may be employed.

However, the method in which the diffusion layer 18 is formed in advance according to the embodiment largely facilitates a manufacturing step for disposing a small-capacity capacitor component, and thus, is suitable for mass production. In other words, ultrasound elements 20 are obtained by manufacturing the ultrasound elements 20 in one silicon wafer and cutting the silicon wafer into pieces. Thus, it is only necessary to faun a diffusion layer on a silicon wafer first in a manufacturing process. Also, the method is particularly preferable because the number of components in the ultrasound unit 30 does not increase.

<Second Embodiment>

An ultrasound unit 30A and an ultrasound endoscope 2A including the ultrasound unit 30A (hereinafter referred to as "ultrasound unit 30A and the like") according to a second embodiment will be described below. Since the ultrasound unit 30A and the like are similar to the ultrasound unit 30 and the like, components having same functions as those of the ultrasound unit 30 and the like are provided with same reference numerals as those of the ultrasound unit 30 and the like and description thereof will be omitted.

Figure 10:
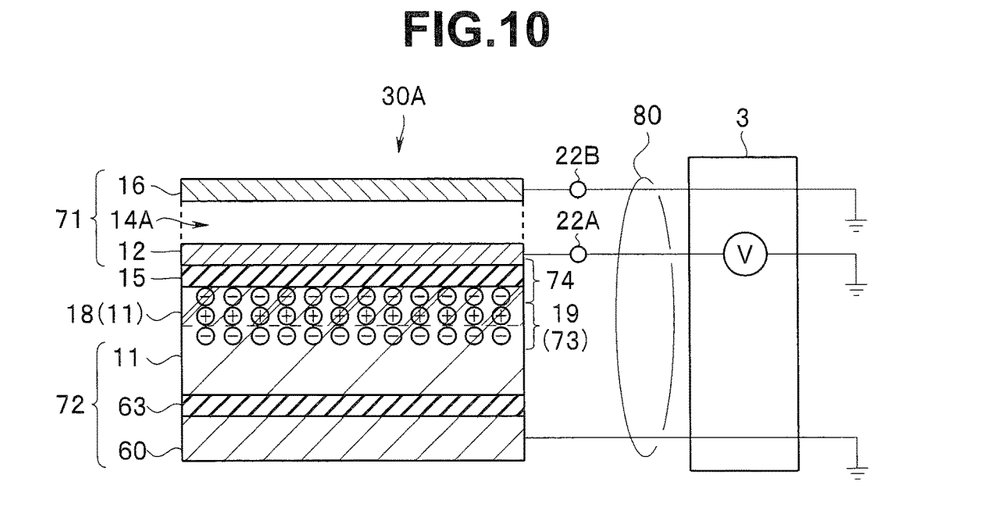
FIG. 10 is a diagram of a configuration of an ultrasound unit according to a second embodiment.

Since the ultrasound unit 30A includes no through holes in an insulation layer 15 of each ultrasound element 20, a lower electrode 12 and a silicon substrate 11 are insulated from each other. Thus, as illustrated in FIGS. 10 and 11, a fourth capacitor 74 (capacity C4) in which an insulation layer 15 serves as a gap is provided.

In the ultrasound unit 30A, upon application of a positive voltage to the lower electrode 12, the insulation layer 15 side of a diffusion layer 18 becomes a negative potential layer, and the opposite side (package member side) becomes a positive potential layer. Thus, as in the ultrasound unit 30, a depletion layer 19 is formed inside the silicon substrate 11. Since the depletion layer 19 has no conductivity, a third capacitor 73 in which the depletion layer 19 serves as a gap is formed.

Figure 11:
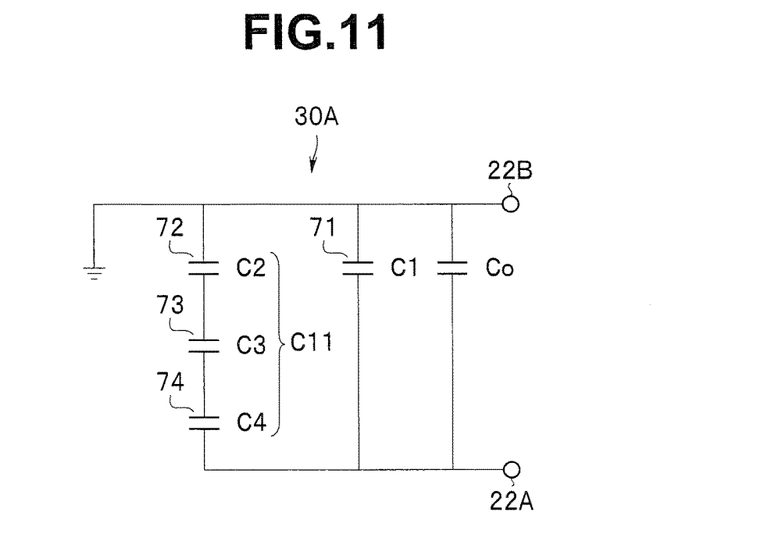
FIG. 11 is a diagram of an equivalent circuit in the ultrasound unit according to the second embodiment.

As illustrated in FIG. 11, the third capacitor 73 and the fourth capacitor 74 are serially connected to a second capacitor 72 having a capacity C2, which is formed as a result of an insulation member 63 serving as a gap, a sum of an overlap capacity Co and the capacities C2, C3 and C4 is a total parasitic capacity Cp. A combined capacity C11 of the second capacitor 72, the third capacitor 73 and the fourth capacitor 74 serially connected can be obtained by C11=(C2×C3×C4)/(C2×C3+C2×C4+C3×C4). If the insulation layer 15 is thin, the capacity C4 of the fourth capacitor 74 is relatively large; however, C2>C11. Here, also, Co is regarded as sufficiently small compared to the other capacities, and it is regarded that Cp=C11; however, implementation of the present invention is not limited to such calculation method as above.

Since the parasitic capacity decreases from C2 to C11, a capacity change rate D (%) measured via external electrodes 22A and 22B when the capacity of the first capacitor 71 changes by ΔC increases from ΔC/(C1+C2) to ΔC/(C1+C11) compared to cases where no third capacitor 73 is formed.

In other words, the ultrasound unit 30A and the like enable provision of effects that are the same as those of the ultrasound unit 30 and the like.

Note that, for example, where the insulation layer 15 is formed so as to be thick to make a capacity between the lower electrode 12 and the substrate 11 be lower than the depletion layer capacity, or where a capacitor having a small capacity that is lower than the depletion layer capacity is disposed at a position partway through a ground potential wire to which a package member 60 is connected, in the embodiments, the diffusion layer 18 having a polarity that is different from that of the substrate 11 is formed so as to form a depletion layer capacity; however, it is possible that such combination is not employed and a diffusion layer having a polarity that is the same as that of the substrate 11 is formed in the substrate.

The present invention is not limited to the above-described embodiments and the like, and various modification and alterations are possible without departing from the spirit of the present invention. Also, the configuration of any of the embodiments and modifications described above may be combined with that of the other embodiments and the like.

What is claimed is:

1. An ultrasound unit comprising:
   ultrasound elements each including a plurality of ultrasound cells formed on a substrate including a semiconductor, the plurality of ultrasound cells each including an upper electrode having a ground potential and a lower electrode to which a drive signal is applied, the upper electrode and the lower electrode being arranged facing each other via a cavity and thereby forming a first capacitor;
   a conductive member in which the plurality of the ultrasound elements are disposed, the conductive member having a ground potential, and
   an insulation member disposed between the conductive member and each of the ultrasound elements,
   a second capacitor being formed as a result of the insulation member serving as a gap,
   wherein a capacity of a third capacitor serially connected to the second capacitor is smaller than a capacity of the second capacitor.

2. The ultrasound unit according to claim 1, wherein:
   the substrate includes, on a surface of the substrate, a diffusion layer having a polarity that is different from a polarity of a parent material of the substrate and having a resistance that is lower than a resistance of the parent material; and
   the third capacitor is formed as a result of a depletion layer serving as a gap, the depletion layer being formed inside the substrate by the diffusion layer.

3. The ultrasound unit according to claim 1, wherein the insulation member includes a backing material that includes an elastic member.

4. The ultrasound unit according to claim 1, wherein (a capacity C3 of the third capacitor)≤(a capacity C2 of the second capacitor×0.5).

5. The ultrasound unit according to claim 1, wherein each of the ultrasound elements includes an insulation layer insulating the substrate and the lower electrode from each other.

6. An ultrasound endoscope comprising:
an insertion portion provided with an ultrasound unit in a distal end portion of the insertion portion, the ultrasound unit including
ultrasound elements each including a plurality of ultrasound cells formed on a substrate including a semiconductor, the plurality of ultrasound cells each including an upper electrode having a ground potential and a lower electrode to which a drive signal is applied, the upper electrode and the lower electrode being arranged facing each other via a cavity and thereby forming a first capacitor,
a conductive member in which the plurality of the ultrasound elements are disposed, the conductive member having a ground potential, and
an insulation member disposed between the conductive member and each of the ultrasound elements, wherein
a second capacitor is formed as a result of the insulation member serving as a gap, and
a capacity of a third capacitor serially connected to the second capacitor is smaller than a capacity of the second capacitor.

7. The ultrasound endoscope according to claim 6, wherein:
the substrate includes, on a surface of the substrate, a diffusion layer having a polarity that is different from a polarity of a parent material of the substrate and having a resistance that is lower than a resistance of the parent material; and
the third capacitor is formed as a result of a depletion layer serving as a gap, the depletion layer being formed inside the substrate by the diffusion layer.

8. The ultrasound endoscope according to claim 7, wherein the insulation member includes a backing material that includes an elastic member.

9. The ultrasound endoscope according to claim 7, wherein (a capacity C3 of the third capacitor)≤(a capacity C2 of the second capacitor×0.5).

10. The ultrasound endoscope according to claim 7, wherein each of the ultrasound elements includes an insulation layer insulating the substrate and the lower electrode from each other.

* * * * *